United States Patent [19]

McGough et al.

[11] Patent Number: 5,015,233

[45] Date of Patent: May 14, 1991

[54] PNEUMATIC INFLATION DEVICE

[75] Inventors: Jeffrey D. McGough, Spencer; Gail L. Brinson, Ellettsville, both of Ind.

[73] Assignee: Freedom Machine, Inc., Ellettsville, Ind.

[21] Appl. No.: 338,741

[22] Filed: Apr. 17, 1989

[51] Int. Cl.[5] .............................................. A61M 5/30
[52] U.S. Cl. ........................................ 604/97; 604/98; 604/70; 604/146; 222/389
[58] Field of Search ............... 604/70, 72, 97–100, 604/131, 140–147, 150, 182, 217, 214; 222/389

[56] References Cited

U.S. PATENT DOCUMENTS

| | | | |
|---|---|---|---|
| 2,687,725 | 8/1954 | Hein, Jr. | 604/70 |
| 2,764,977 | 10/1956 | Ferguson | 604/70 |
| 2,785,678 | 3/1957 | Hein, Jr. | 604/70 |
| 2,960,087 | 11/1960 | Uytenbogaart | 604/144 |
| 3,720,201 | 3/1973 | Ramsey, III . | |
| 3,768,472 | 10/1973 | Hodash et al. | 604/143 |
| 3,863,504 | 2/1975 | Borsanyi . | |
| 3,945,379 | 3/1976 | Pritz et al. | 604/70 |
| 4,250,887 | 2/1981 | Dardik et al. | 604/150 |
| 4,332,254 | 6/1982 | Lundquist . | |
| 4,370,982 | 2/1983 | Reilly . | |
| 4,426,024 | 1/1984 | Hogan et al. | 604/141 |
| 4,437,859 | 3/1984 | Whitehouse et al. | 604/131 |
| 4,439,185 | 3/1984 | Lundquist | 604/97 |
| 4,509,523 | 4/1985 | Pevsner . | |
| 4,654,027 | 3/1987 | Dragan et al. | 604/99 |
| 4,655,749 | 4/1987 | Fischione . | |
| 4,727,887 | 3/1988 | Haber . | |
| 4,790,821 | 12/1988 | Stines . | |
| 4,944,726 | 7/1990 | Hilal et al. | 604/143 |

FOREIGN PATENT DOCUMENTS

| | | | |
|---|---|---|---|
| 3640378 | 6/1988 | Fed. Rep. of Germany | 604/98 |
| 33043 | 6/1928 | France | 604/131 |
| 1271524 | 11/1986 | U.S.S.R. | 604/70 |

*Primary Examiner*—Stephen C. Pellegrino
*Assistant Examiner*—Ralph A. Lewis
*Attorney, Agent, or Firm*—Barnes & Thornburg

[57] ABSTRACT

This invention relates to an apparatus for driving a syringe plunger into a barrel using manually created pneumatic pressure that is useful for inflating medical devices such as angioplaty balloons. The apparatus permits one handed, highly controlled application of pressure to a standard medical syringe.

8 Claims, 2 Drawing Sheets

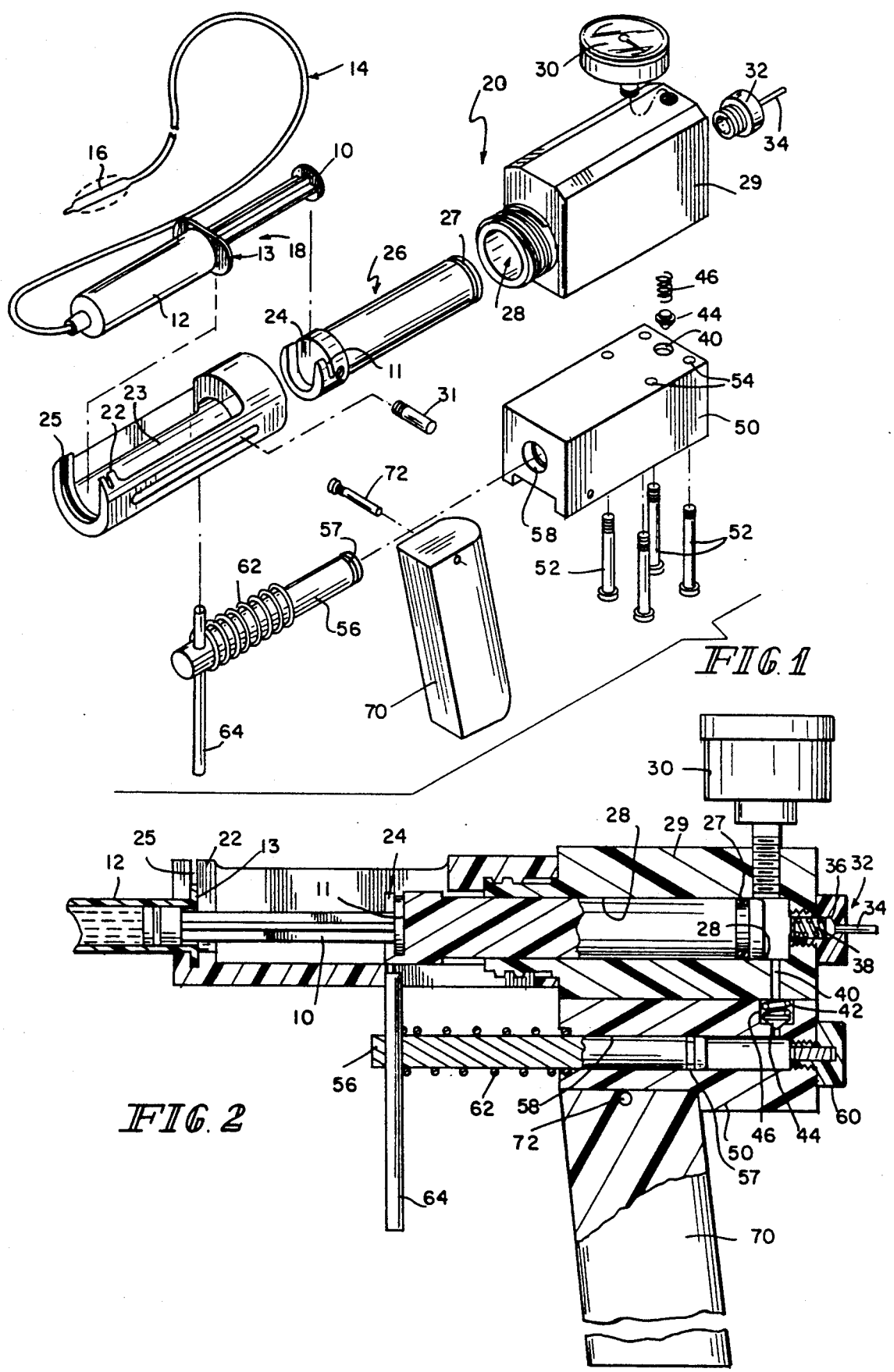

PNEUMATIC INFLATION DEVICE

BACKGROUND AND SUMMARY OF THE INVENTION

This invention relates to an apparatus for driving a syringe plunger into a barrel using manually created pneumatic pressure.

Many useful medical procedures and devices require the application of a controlled and sustained pressure. Medical devices such as angioplasty balloons, esophageal dilatation balloons, artificial urethral sphincters, and skin expanders all require the application of a sustained pressure that is both easy to apply and highly controllable.

Devices suitable for applying pressure to medical devices suffer from a number of disadvantages, including complexity, necessity of two handed operation, and the difficulty of precisely controlling the amount of pressure applied while using a standard medical syringe.

Fischione (U.S. Pat. No. 4,655,749) discloses an angioplasty pressure controller having a housing with a slidable pressure cylinder. A drive screw is connected to a piston in the cylinder and arranged for fine adjustment by turning the drive screw. This device has the disadvantage that two handed operation is required to operate the device.

Lundquist (U.S. Pat. No. 4,332,254) discloses a system for inflation and deflation of a balloon-type dilating catheter assembly utilized to perform percutaneous transluminal coronary angioplasty procedures. A primary syringe pump drives a secondary fluid pump mounted on the primary pump. The device has the disadvantage in that standard medical syringes cannot be used to supply an easily controllable, sustained pressure utilizing one-handed pumping operation. Reference is made to this prior art concerning the applicability of such apparatus in medical fields.

The present invention is an improvement over devices known in the prior art because inflation of medical devices requiring the application of pressure in excess of what is easily achievable for a sustained period of time by unaided manual force applied to a plunger in a syringe having a pressurizing fluid contained within its barrel are enabled by use of this apparatus.

An apparatus according to the present invention comprises means for holding a syringe barrel and means for holding an associated syringe plunger. A manually operated pneumatic driving means is used to apply force to the syringe plunger. The pneumatic driving means comprises a drive piston reciprocable in a sealed drive piston chamber. The drive piston is directly or through appropriate linkages capable of applying a sustained force to the syringe plunger.

A pumping system useful for incrementally increasing the pneumatic pressure in the drive cylinder chamber, and therefore also incrementally increasing the force applied by the drive piston to the syringe plunger, comprises a manually driven pumping piston capable of reciprocating action in a pumping chamber of a pumping chamber body. Air compressed by the action of the pumping piston during a compression stroke can travel through a pneumatic passage containing a unidirectional valve which only permits the outlet of pressurized air from the pumping chamber. The unidirectional valve between the pumping chamber and the cylinder chamber permits the gradual increase of pneumatic pressure in the cylinder chamber by repeated compressions of the manually driven pumping piston. This system gives the user excellent control over the amount of pressure applied to an inflatable medical device and the speed at which the pressure is applied. Both fast and slow inflation is enabled by a respective fast or slow manual pumping action.

The pumping piston has a connected piston handle for manually driving the piston into the pumping chamber. Entrained air is compressed to a pressure sufficient to open the unidirectional valve and allow pressurization of the drive piston chamber. The pumping piston is spring loaded to return the piston to an extended position in preparation for the next compression stroke. Additional air is admitted to the pumping chamber through an air intake valve or opening which closes on the compression stroke of the piston and opens on a return stroke during which the piston is retracted from the pumping chamber.

BRIEF DESCRIPTION OF THE DRAWINGS

The apparatus of this invention will be better understood with reference to the following detailed drawings:

FIG. 1 is an exploded, perspective view of a pneumatic inflation device according to the present invention, with a standard syringe connected to a balloon catheter also shown;

FIG. 2 is a cross-sectional view of the present device perpendicularly oriented.

DESCRIPTION OF THE PREFERRED EMBODIMENTS

Figure 3:
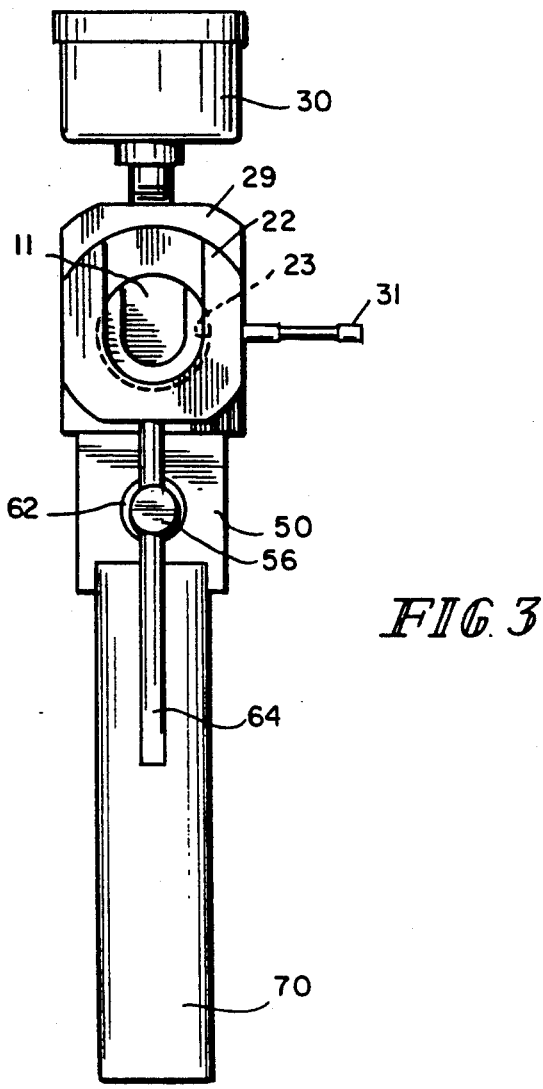
FIG. 3 is an end view thereof.

Referring to the drawings, an illustrative embodiment of the present invention comprises a pneumatic driver 20 suitable for driving a syringe plunger 10 into a syringe barrel 12 of a standard medical syringe 18. The syringe barrel 12 in operation would contain a fluid (not shown) capable of expanding or inflating a balloon 16 of a balloon catheter 14.

The syringe 18 is fixably held by the pneumatic driver 20 through the action of a syringe barrel holding means 22 and a syringe plunger holding means 24. In the embodiment shown in the illustrations, the holding means 22 comprises a barrel tip 25 slotted to accept the syringe barrel 12 and the associated syringe wings 13 of a standard disposable syringe 18. The syringe plunger holding means 24 in the illustrative embodiment also utilizes a syringe plunger slot 11 to retain the syringe plunger 10.

Extending between the syringe barrel holding means 22 and the syringe plunger holding means 24 is a syringe plunger trough 23 having a length no greater than the length of the syringe plunger 10. The trough 23 acts as a spacer between the syringe barrel holding means 22 and the syringe plunger holding means 24, having sufficient length and tensile strength to permit application of a force to the syringe plunger 10. Alternative embodiments are also possible, subject to the requirement that the syringe barrel holding means 22 and the syringe plunger holding means 24 are held at an essentially fixed distance apart from each other under the normal operating forces likely to be encountered during use of the apparatus of the present invention.

The holding means 24 is removably connected to a drive piston 26. The drive piston 26 is reciprocably disposed for at least a portion of its length in a cylinder chamber 28 formed from the interior of a drive piston chamber body 29. The drive piston 26 has a drive piston 0-ring 27, which encircles and pneumatically seals the portion of drive piston 26 disposed in the cylinder chamber 28.

A mechanical advantage is realized by the choice of radial diameter of the syringe plunger 10 and the drive piston 26. In the embodiment shown, the radial diameter of the drive piston chamber 29 is selected to give a drive piston 26 area twice the area of the syringe plunger 10. This gives a 2:1 mechanical advantage that increases the pressure applied by the syringe 18 to a balloon catheter 14.

The pneumatic pressure within the drive piston chamber 28 can be measured by a pressure gauge 30 in fluid communication with the drive piston chamber 28. The pressure gauge 30 can have a readout calibrated to directly measure the pneumatic pressure within the drive piston chamber 38, or can in a preferred embodiment be calibrated to display an internal pneumatic pressure of the balloon catheter 14, which is generally a linear function of the pressure in drive piston chamber 28.

A manually actuated pressure relief valve 32 for relieving pneumatic pressure in drive piston 28 is also provided. In the illustrative preferred embodiment the relief valve 32 is sited in the drive piston chamber 29 body in an axially aliqned position opposite the drive piston 26. This positioning permits the drive piston 26 to completely fill the drive piston chamber 28 by release of the displaced air through the pressure relief valve 32 upon actuation of manual plunger 34.

High pressure air is admitted to drive piston chamber 28 through a pneumatic passage 40. In the illustrated embodiment a unidirectional valve 42 is situated within the pneumatic passage 40. The unidirectional valve 42 acts to admit into the drive piston chamber 28 only air having a higher pneumatic pressure than the air within the drive piston chamber 28. A valve 46, having an upper and lower surface, freely movable in the pneumatic passage 40, is kept in a pneumatically tight position by the pneumatic pressure exerted against the upper surface by the pneumatic pressure in drive piston chamber 28. When the pneumatic pressure exerted against the lower surface of valve 46 exceeds the combined force of the pneumatic pressure on the upper surface of the valve 46 and the force exerted by a spring 38, the valve opens to admit higher pressure air into the drive piston chamber 28. Upon equalization of pneumatic pressure between the drive piston chamber 28 and an external pneumatic pressure source, the force exerted by the spring 38 acts to close the valve 44.

In the embodiment illustrated, the external pressure source comprises a pumping chamber body 50, removably fixed to the drive piston chamber body 29 by bolts 52 passing through boltholes 54 in the pumping chamber body 50. The pumping chamber body 50 has an internal, cylindrical pumping chamber 58 into which a pumping piston 56 can be reciprocably axially disposed for at least a portion of its length.

The pumping piston 56 is fitted with an O-ring 57 to pneumatically seal the pumping chamber 58 when the piston 56 is inserted into the pumping chamber body 50. The piston 56 is also fitted with a piston handle 64 suitable for manual grasping. In operation, a compression stroke is initiated by a manually exerted force that moves the piston 56 into the pumping chamber 58. This increases the pneumatic pressure in the chamber 58 until the force exerted by the air exceeds the force necessary to actuate the unidirectional valve 42 and release the high pressure air into the chamber 28.

After the pneumatic pressure has equalized between the drive piston chamber 28 and the pumping chamber 58, closing the unidirectional valve 42, the pumping piston 56 is projected from the pumping chamber 58. In the illustrated embodiment, a spring 62, helically wound about the piston 56 and axially situated between the piston handle 64 and the pumping piston O-ring 57 automatically forces retraction of the piston 56 from the chamber 58 when the manually exerted force on piston handle 64 does not exceed the force exerted by the spring 62.

Figure 4:
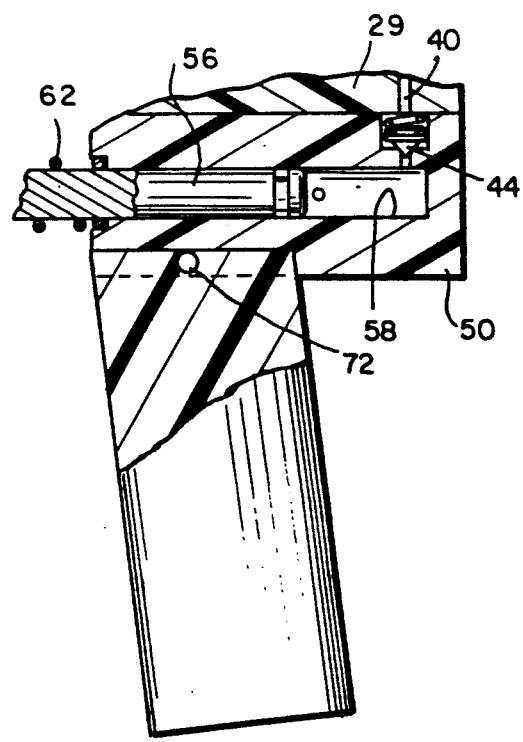
FIG. 4 is a partial view showing the pumping piston and airhole in a pumping piston chamber body.

To prevent drawing a vacuum in the pumping chamber 58 that would inhibit the retraction of the pumping piston 56, an air intake valve 60 situated in the pumping chamber body 50 is provided. The admitted air can also be a pneumatic pressure source for repeat compression strokes. The air intake valve 60 is ideally sited axially in the pumping chamber, opposite to the pumping piston 56. The valve should only admit air into the pumping chamber 58, and prevent the outlet of air during the compression stroke. A suitable one-way air valve design for the air intake valve 60 is similar to the unidirectional valve 42. It will also be appreciated that the valve 60 may be replaced by a simple small air hole 68 in the body 50, which is opened and closed by the movement of the piston 58, and is shown in FIG. 4.

Manually gripping the apparatus is facilitated by a pistol grip 70 affixed by bolt 72 to the pumping chamber body 50 in an orientation substantially parallel to the piston handle 64. The pistol grip 70 permits one-handed use of the apparatus to increase the pneumatic pressure applied to a balloon catheter 14. The apparatus can be manually grasped by one hand, and the piston handle 64 brought toward the pistol grip 70 initiating the compressive stroke, and the increase in pressure applied to the balloon catheter 14 easily read from the pressure gauge 30 mounted atop the apparatus.

It will be appreciated by those skilled in the art that alternative non-manual pressurizing means can substitute for hand action. For example, a foot pedal (not shown) can be used to initiate a compressive stroke. The foot pedal can be either a separate unit connected by a pressure line to the drive piston chamber 38, or formed contiguous to the drive piston chamber body 29.

The illustrated embodiment of the present invention can be easily disassembled to simplify cleaning, maintenance, and replacement of parts of the apparatus. The plunger trough 23 can be screwably disconnected from the drive piston chamber body 28, the drive piston chamber body 29 can be separated from the pumping chamber body 50 by removal of the bolts 52, and the pistol grip 70 can be separated from the pumping chamber body 50 after removal of bolt 72. Since both the drive piston 26 and the pumping piston 56 are freely movable within their respective chamber, the disconnection of the plunger trough 23 allows the withdrawal of both the drive piston 26 and piston 56 for cleaning, lubrication, or replacement.

What is claimed is:

1. A driver for a syringe having a syringe barrel and a syringe plunger, said driver comprising
barrel holding means for holding said syringe barrel,
plunger holding means for holding said syringe plunger at least partially within said syringe barrel, the plunger holding means being movable with respect to the barrel holding means, a pneumatic driver including a drive piston positioned at least partially in a drive piston chamber defined by a drive piston chamber body, with said drive piston being connected to said plunger holding means, and pumping means for repeatedly pumping air into the drive piston chamber through a pneumatic passage containing a unidirectional valve that only permits airflow from said pumping means into the drive piston chamber, the pumping means including a manually driven element situated for reciprocating movement in a chamber connected to the pneumatic passage to transiently increase pneumatic pressure in the pneumatic passage and open the unidirectional valve.

2. A driver for a syringe having a syringe barrel and a syringe plunger, said driver comprising barrel holding means for holding said syringe barrel, plunger holding means for holding said syringe plunger at least partially within said syringe barrel, the plunger holding means being movable with respect to the barrel holding means, a pneumatic driver including a drive piston positioned at least partially in a drive piston chamber defined by a drive piston chamber body, with said drive piston being connected to said plunger holding means, and pumping means for repeatedly pumping air into the drive piston chamber through a pneumatic passage containing a unidirectional valve that only permits airflow from said pumping means into the drive piston chamber, the pumping means being situated adjacent to the pneumatic driver and including a pumping chamber body defining a pumping chamber, an air inlet valve for admitting air into the pumping chamber, and a pumping piston positioned for reciprocating movement in the pumping chamber to compress entrained air.

3. An apparatus according to claim 2 wherein the pumping piston is attached to a handle in manually squeezable opposition to said pistol grip so that movement of the handle toward said pistol grip acts to drive the pumping piston into the pumping chamber.

4. The invention of claim 3 in which said drive piston and said pumping piston are set in parallel spaced apart relationship with said drive piston disposed above said pumping piston and said barrel holding means and said plunger holding means being arranged generally to lie in coaxial relationship to the drive piston.

5. The invention of claim 4 wherein a pressure gauge is placed in fluid connection with said drive piston chamber to indicate the pneumatic pressure.

6. The invention of claim 5 wherein a release valve in fluid communication with the drive piston chamber is provided to control relief of pneumatic pressure in the drive piston chamber.

7. The invention of claim 6 wherein said barrel holding means, said plunger holding means, the pneumatic driver, and the pumping means can be separated from each other to facilitate cleaning.

8. A pneumatic drive for a syringe having a syringe barrel and a syringe plunger reciprocable in said barrel, said driver comprising barrel holding means for holding said syringe barrel having a trough with an end formed to accept the syringe barrel, plunger holding means for holding said syringe plunger at least partially within said syringe barrel, the plunger holding means being movable with respect to the barrel holding means, a pneumatic driver coupled to said plunger holding means, said pneumatic driver including a drive piston at least partially disposed in a drive piston chamber defined by a drive piston chamber body, a pressure relief valve to control pressure relief in the drive piston chamber, a pressure gauge in fluid communication with said drive piston chamber to measure pneumatic pressure in said drive piston chamber, and a pneumatic passage in fluid communication with the drive piston chamber further having a unidirectional valve for admitting air at a higher pressure than air contained in the drive piston chamber into the drive piston chamber, and a pneumatic pump for supplying air under pressure to said drive piston chamber including a pumping chamber body defining a pumping chamber, a pumping piston reciprocably disposed in the pumping chamber, a handle connected to said pumping piston, a pistol grip attached to said pumping chamber body so that manual squeezing action between said handle and piston grip acts to compress entrained air in said pumping chamber, with said pumping chamber being in fluid communication with said drive piston chamber through said pneumatic passage, said fluid communication limited by said unidirectional valve.

* * * * *